United States Patent
Balooch et al.

(10) Patent No.: US 11,127,176 B2
(45) Date of Patent: Sep. 21, 2021

(54) SYSTEMS AND METHODS FOR VISUALIZING FUTURE SKIN TRENDS BASED ON BIOMARKER ANALYSIS

(71) Applicant: L'Oreal, Paris (FR)

(72) Inventors: Guive Balooch, New York, NY (US); Edouard Messager, Saint-Ouen (FR); Aude Foucher, Aulnay-sous-Bois (FR); Nukhet Cavusoglu, Claye-Souilly (FR); Ji Lee, New York, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/264,181

(22) Filed: Jan. 31, 2019

(65) Prior Publication Data

US 2020/0250866 A1     Aug. 6, 2020

(51) Int. Cl.
*G06T 11/20* (2006.01)
*G16H 10/20* (2018.01)
*G16H 10/40* (2018.01)
*G16H 50/20* (2018.01)

(52) U.S. Cl.
CPC ........ *G06T 11/206* (2013.01); *G06T 2210/41* (2013.01)

(58) Field of Classification Search
CPC ................ G06T 11/206; G06T 2210/41
See application file for complete search history.

(56) References Cited

U.S. PATENT DOCUMENTS

| 9,251,609 | B1 * | 2/2016 | Wang | G06T 11/206 |
| 2009/0245603 | A1 * | 10/2009 | Koruga | A61B 5/445 382/128 |
| 2010/0254581 | A1 | 10/2010 | Neeser et al. | |
| 2015/0099947 | A1 * | 4/2015 | Qu | A61B 5/442 600/306 |
| 2015/0149318 | A1 * | 5/2015 | Khoo | G06Q 30/0631 705/26.7 |
| 2017/0084069 | A1 * | 3/2017 | Kim | G06T 11/60 |
| 2019/0078162 | A1 * | 3/2019 | Reis de Oliveira | C12Q 1/6883 |

FOREIGN PATENT DOCUMENTS

| WO | 2018/109078 A1 | 6/2018 |
| WO | 2018/115517 A1 | 6/2018 |
| WO | 2019/038290 A1 | 2/2019 |

OTHER PUBLICATIONS

International Search Report and Written Opinion dated May 19, 2020, issued in corresponding International Application No. PCT/US2020/016214, filed Jan. 31, 2020, 28 pages.

* cited by examiner

*Primary Examiner* — Sing-Wai Wu

(74) *Attorney, Agent, or Firm* — Christensen O'Connor Johnson Kindness PLLC (57) ABSTRACT

Systems, methods, and devices are provided for generating visualizations of facial aging trends based on protein biomarker concentration information. Protein biomarker concentration information is generated by an immunoassay analyzer device. The protein biomarker concentration information is used to predict one or more facial aging trends, such as shiny skin, rough skin, uneven skin tone, eye wrinkles, photo-aging, loss of elasticity, or dilated pores. A visualization, such as a spider diagram or a face aging simulation, is generated and presented.

17 Claims, 5 Drawing Sheets

SYSTEMS AND METHODS FOR VISUALIZING FUTURE SKIN TRENDS BASED ON BIOMARKER ANALYSIS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a method of generating a facial aging visualization implemented by at least one computer processor programmed by one or more machine instructions is provided. At least one instance of a predicted facial aging trend is determined based on receiving protein biomarker concentration information. A virtual representation is generated on an electronic display indicative of the predicted facial aging trend.

In some embodiments, a system for generating a facial aging visualization is provided. The system comprises circuitry for determining at least one instance of a predicted facial aging trend based on receiving protein biomarker concentration information; and circuitry for generating a virtual representation on an electronic display indicative of the predicted facial aging trend.

In some embodiments, a computing device is provided. The computing device is configured to determine at least one instance of a predicted facial aging trend based on receiving protein biomarker concentration information; and generate a virtual representation on an electronic display indicative of the predicted facial aging trend.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The medical field is currently being improved by the growing availability of biomarker analysis systems. These systems, which can operate in an outpatient or clinical setting, can provide a noninvasive measurement of various protein concentrations. These protein concentrations may then be used for various treatment-related purposes. Through clinical studies, certain proteins that can be detected by these biomarker analysis systems have been identified to be linked to clinical signs of aging, as well as responsiveness/non-responsiveness to various active ingredients of skincare products. For example, preliminary studies have suggested that biomarkers such as YKL40, TG3, LCN1, IDE, and FLG2 may be correlated with clinical signs of aging and responsiveness such as shiny skin, rough skin, uneven skin tone, eye wrinkles, photo aging, loss of elasticity, dilated pores, responsiveness to retinol, and responsiveness to proxylane.

Even though these correlations have been suggested, the biomarker analysis system only provides raw protein concentration information, and does not use these correlations. What is desired are systems and methods that visualize future skin trends based on biomarker concentration information in order to improve the utility of the information gathered by the biomarker analysis system, particularly in determining a recommended skincare regimen to address the future trends predicted based on the detected biomarkers.

Figure 1:
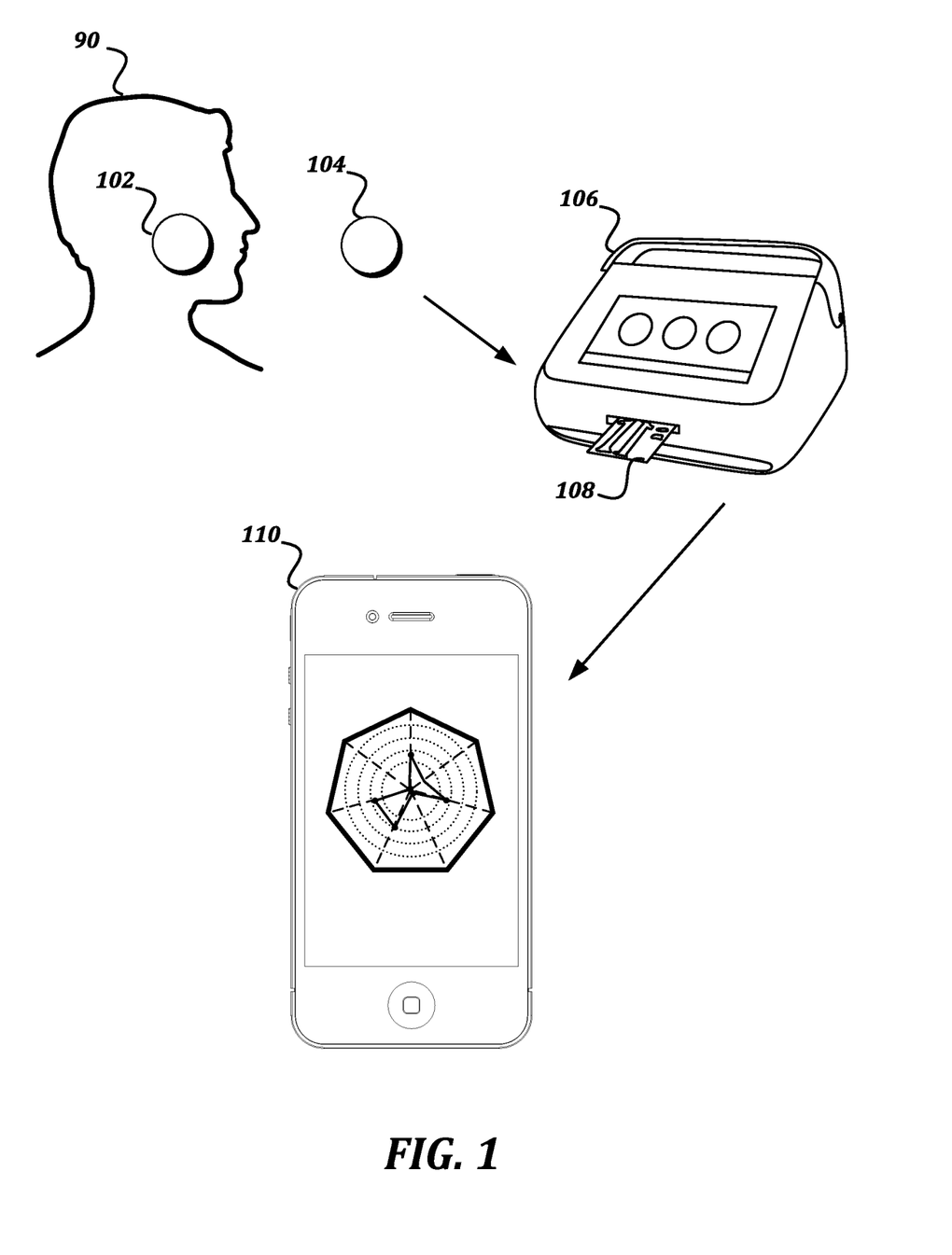
FIG. 1 is a high-level schematic drawing that illustrates various components of an example embodiment of a system according to various aspects of the present disclosure.

FIG. 1 is a high-level schematic drawing that illustrates various components of an example embodiment of a system according to various aspects of the present disclosure. The system is used to obtain a sample from a user 90, and to generate skin trend visualizations based on the sample. As shown, one or more sampling disks 102, 104 are used to obtain a sample from the user 90. A sampling disk 104 is then processed by a protein extraction device 208, and a collected sample is applied to a test cartridge 108. The test cartridge 108 is inserted into an immunoassay analyzer device 106. The immunoassay analyzer device 106 determines concentrations of various protein biomarkers that are associated with various skin trends. The protein biomarker concentration information is then provided to a trend visualization computing device 110, which generates and presents skin trend visualizations based on the protein biomarker concentration information.

Figure 2:
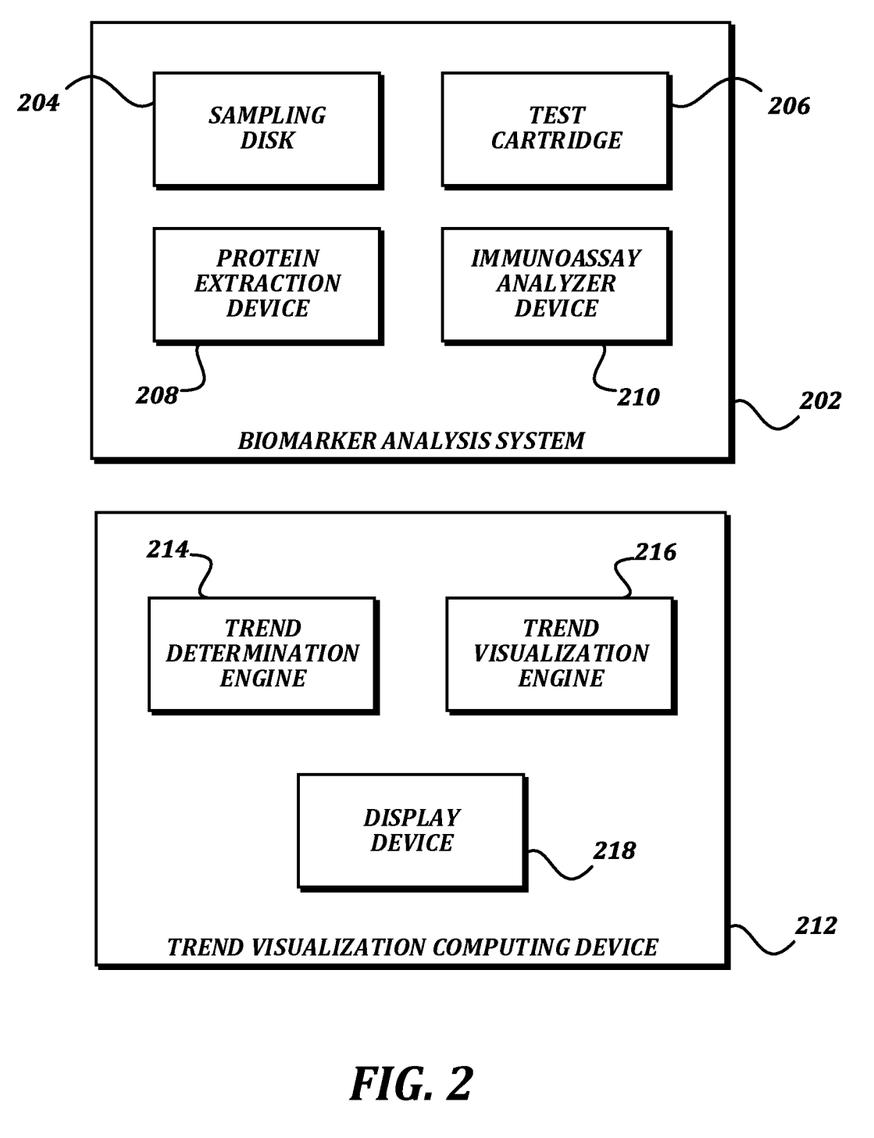
FIG. 2 is a block diagram that illustrates further details of an example embodiment of a biomarker analysis system and an example embodiment of a trend visualization computing device according to various aspects of the present disclosure.

FIG. 2 is a block diagram that illustrates further details of an example embodiment of a biomarker analysis system and an example embodiment of a trend visualization computing device according to various aspects of the present disclosure.

In some embodiments, the biomarker analysis system 202 includes one or more devices that provide a measurement of biomarkers sampled from a subject. In some embodiments, such sampling is done quickly and non-invasively, thus allowing the biomarker sampling to take place in an outpatient clinical or retail environment. In the illustrated embodiment, the biomarker analysis system 202 includes a sampling disk 204, a test cartridge 206, a protein extraction device 208, and an immunoassay analyzer device 210.

In some embodiments, the sampling disk 204 comprises a substrate and an adhesive. The adhesive is suitable for removably attaching the sampling disk 204 to the skin of a subject and obtaining a sample of skin cells therefrom. Though a sampling disk 204 is described, in some embodiments, an adhesive device of another shape, including but not limited to a rectangle or a tape may be used. In some embodiments, a swab, a wipe, or another device usable to collect a skin cell sample may be used instead of an adhesive device. One non-limiting example of a device that is suitable for use as a sampling disk 204 is a D-SQUAME® sampling disk produced by CuDerm Corporation, though other devices could be used.

In some embodiments, the protein extraction device 208 is configured to remove samples from sampling disks 204 and convert them into a form that can be provided to a test cartridge 206 for processing. In some embodiments, the protein extraction device 208 may include a container in which the sampling disk 204 may be placed along with a buffer solution. The protein extraction device 208 may also include a device for agitating, centrifuging, or otherwise processing the container such that the proteins from the collected skin sample are released from the sampling disk 204 and dissolved in the buffer solution.

In some embodiments, the test cartridge 206 is approximately the size of a credit card, and includes an inlet in which a droplet (approximately 30 μl) of the solution containing the proteins from the collected skin sample may be placed. The inlet may be coupled to one or more microfluidic channels through which the solution will automatically flow. In some embodiments, antibodies may be deposited within the one or more microfluidic channels, and antigens within the sample may react with the antibodies. This reaction may cause fluorescent beads associated with the antibodies to fluoresce according to the concentrations of the proteins being measured. The immunoassay analyzer device 210 may accept the test cartridge 206, and may measure the concentrations of the proteins of interest within the sample. In some embodiments, the immunoassay analyzer device 210 may do so by using laser light to determine which fluorescent beads are fluorescing. Once measured, the immunoassay analyzer device 210 may provide the determined protein concentrations to other components of the system using any suitable technique, including but not limited to presenting the protein concentrations on a display, printing the protein concentrations on a paper receipt, and electronically transmitting the determined protein concentrations to another device. One non-limiting example of an immunoassay analyzer device 210 (and its associated test cartridges 206) are the FREND™ System provided by NanoEnTek Inc. In some embodiments wherein the determined protein concentrations are electronically transmitted, the electronic transmission may be encrypted and/or anonymized in order to protect the privacy of the information.

The trend visualization computing device 212 is a computing device configured to receive protein concentration information from the biomarker analysis system 202, determine one or more skin trends based on the protein concentration information, and present visualizations based on the one or more skin trends. In some embodiments, the trend visualization computing device 212 may be a mobile computing device such as a smartphone or a tablet computing device. In some embodiments, the trend visualization computing device 212 may be a desktop computing device or a laptop computing device. In some embodiments, the trend visualization computing device 212 may include more than one computing device, such as a user computing device configured to provide a user interface and one or more server computing devices configured to provide computational functionality (such as the functionality of the trend determination engine 214 and/or the trend visualization engine 216 described below). In such embodiments, the user computing device and the one or more server computing devices may communicate via any suitable communication technology or technologies, such as a wired technology (including but not limited to Ethernet, USB, or the Internet) or a wireless technology (including but not limited to WiFi, WiMAX, 3G, 4G, LTE, or Bluetooth).

As illustrated, the trend visualization computing device 212 includes a trend determination engine 214, a trend visualization engine 216, and a display device 218.

In some embodiments, the trend determination engine 214 is configured to receive protein biomarker concentration information from the biomarker analysis system, and to determine skin trends using the correlation information that has been clinically determined. In some embodiments, the trend visualization engine 216 is configured to generate virtual representations of skin trends based on the skin trends determined by the trend determination engine 214. In some embodiments, the display device 218 is used to present the virtual representations of skin trends generated by the trend visualization engine 216. In some embodiments, the display device 218 may be a touch-sensitive display, and may also be used to accept input from a user to a user interface. Further details of the functionality of the components of the trend visualization computing device 212 are provided below.

In general, the word "engine," as used herein, refers to logic embodied in hardware or software instructions, which can be written in a programming language, such as C, C++, COBOL, JAVA™, PHP, Perl, HTML, CSS, JavaScript, VBScript, ASPX, Microsoft .NET™, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

Figure 3:
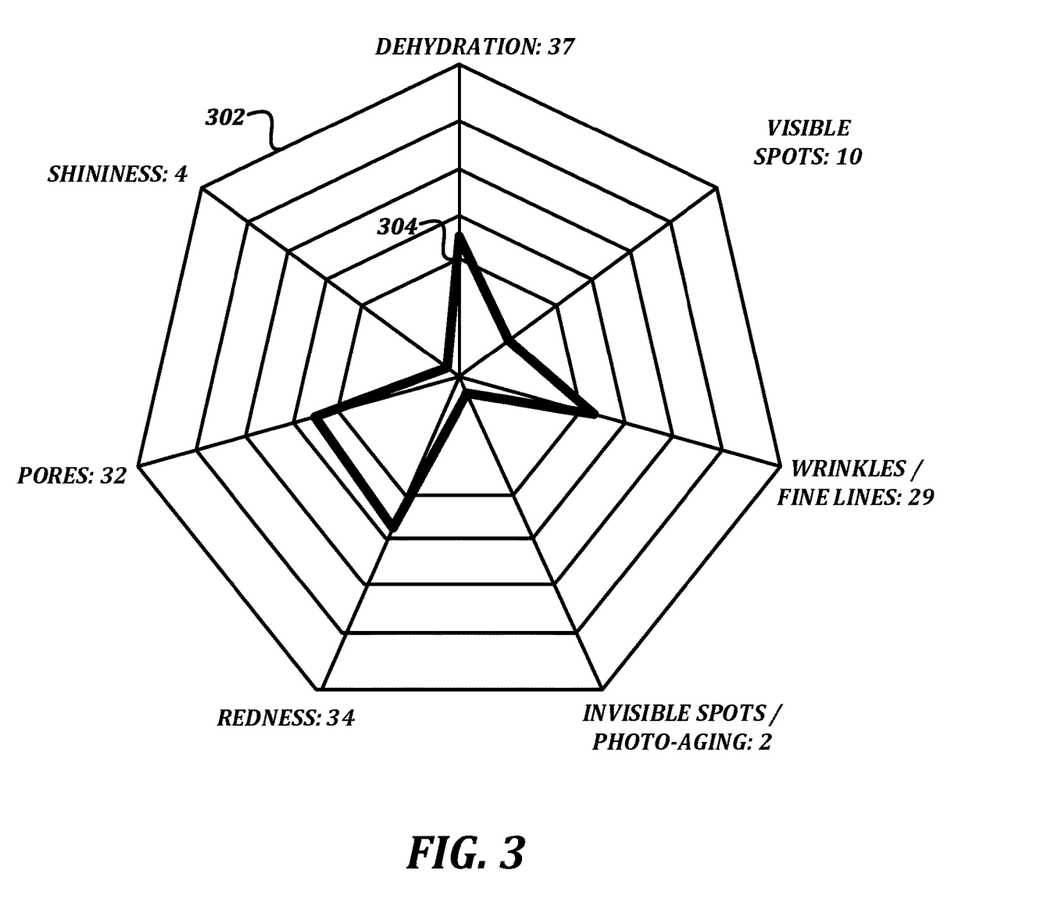
FIG. 3 is an illustration of an example embodiment of a virtual representation created according to various aspects of the present disclosure.

FIG. 3 is an illustration of an example embodiment of a virtual representation created according to various aspects of the present disclosure. In the illustration, a spider diagram 302 is shown that illustrates the likelihood of a set of skin conditions. As shown, the spider diagram 302 includes scales for shininess, dehydration, visible spots, wrinkles/fine lines, invisible spots/photo-aging, redness, and pores. A dot is placed on each scale, and the dots are connected by a line 304 to illustrate how far along each scale the skin trends are predicted to extend. In some embodiments, the dots and the line 304 indicate an amount of each skin condition that is detected at a given point in time, and a slider or other user interface element may be provided to allow a user to explore how the skin conditions are predicted to change over time. In some embodiments, the dots and the line 304 indicate a rate of change of each skin condition. In some embodiments, the visualization may include selections for various skin treatment regimens, and the trend visualization engine 216 may update the trend visualization based on the biomarker concentration information and the selected skin treatment regimen so that the user can evaluate the effects of various skin treatment regimens.

The illustrated spider diagram 302 is a non-limiting example of a trend visualization or virtual representation. In some embodiments, other types of trend visualizations or virtual representations may be provided. For example, in some embodiments, similar information may be provided using numerical scales for each skin condition in a table (such as a shininess value from 0-100, a dehydration value from 0-100, etc.). As another example, a photo of the subject may be obtained, and the virtual representation may use a photo filter to alter the photo based on one or more of the predicted skin trends.

Figure 4:
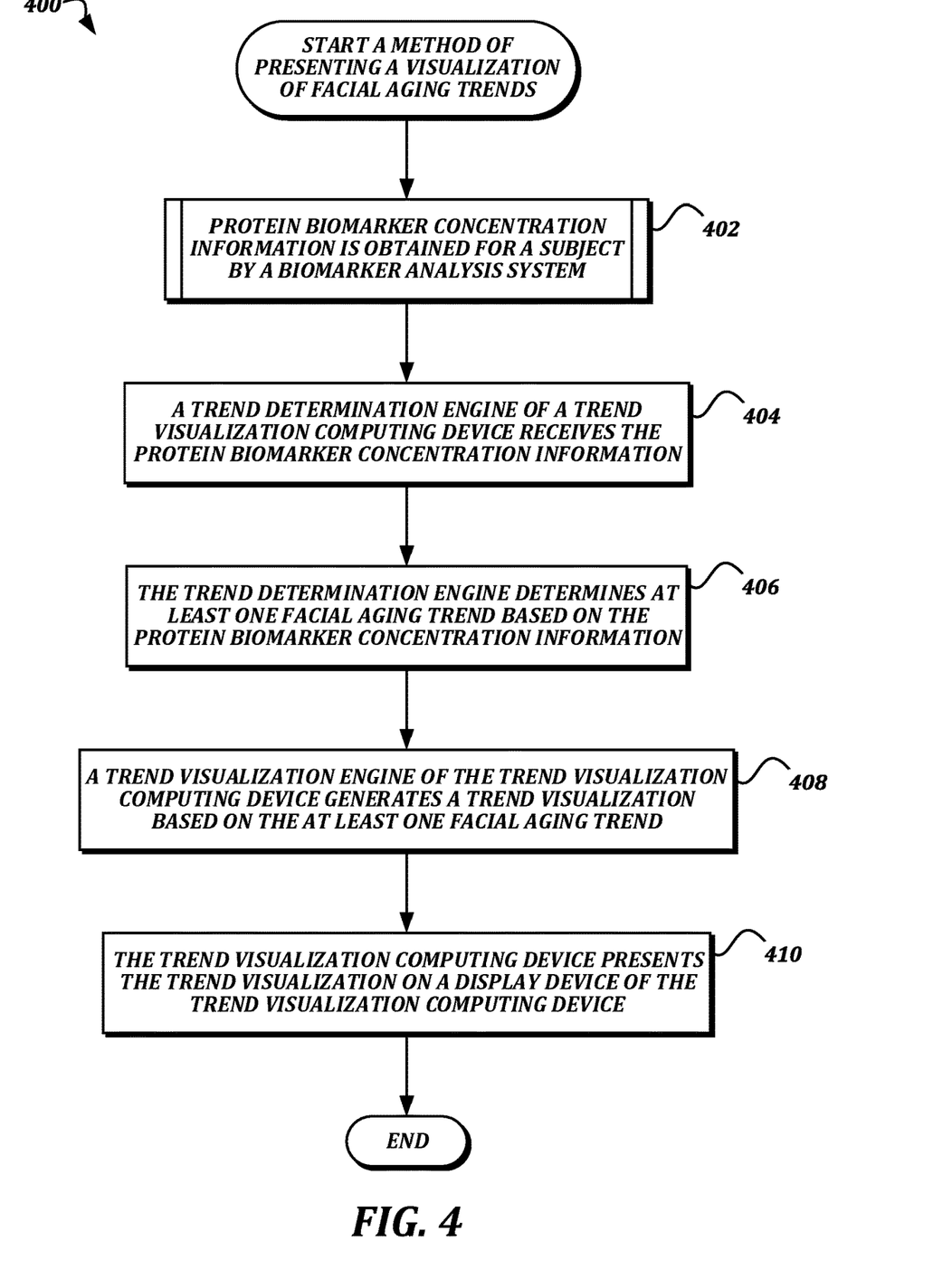
FIG. 4 is a flowchart that illustrates an example embodiment of a method of presenting a visualization of facial aging trends according to various aspects of the present disclosure.

FIG. 4 is a flowchart that illustrates an example embodiment of a method of presenting a visualization of facial aging trends according to various aspects of the present disclosure. From a start block, the method 400 advances to procedure block 402, where a procedure is executed wherein protein biomarker concentration information is obtained for a subject by a biomarker analysis system 202. A non-limiting example of a biomarker analysis system 202 is illustrated in FIG. 2 and discussed above. Any suitable procedure may be used to collect the protein biomarker concentration information, including but not limited to the procedure 500 illustrated in FIG. 5 and described below.

Next, at block 404, a trend determination engine 214 of a trend visualization computing device 212 receives the protein biomarker concentration information. In some embodiments, the protein biomarker concentration information is received from the biomarker analysis system 202 by the trend determination engine 214 via a network. The network may be a wireless network, including but not limited to a Wi-Fi network, a cellular network (including but not limited to a 3G network, a 4G network, a 5G network, or an LTE network), or a Bluetooth network; a wired network, including but not limited to an Ethernet network, a USB network, or a FireWire network; and/or any other type of network. In some embodiments, the protein biomarker concentration information may be displayed by a display device (not illustrated) of the biomarker analysis system 202, and the protein biomarker concentration information may be manually entered into an interface associated with the trend visualization computing device 212.

At block 406, the trend determination engine 214 determines at least one facial aging trend based on the protein biomarker concentration information. Preliminary clinical studies have suggested linkage between five biomarkers (FLG2, TG3, IDE, LCN1, and YKL40) and clinical signs of aging. Example predictive performances (ROC curves) of these biomarkers for various clinical signs of aging are as follows:

| Clinical Sign | Biomarker | p value | Accuracy | Sensitivity | Specificity | kappa | Cutt off (ng/ml) |
|---|---|---|---|---|---|---|---|
| Shiny skin | FLG2 | 0.0000 | 66% | 77% | 53% | 0.30 | <166.3 |
| Rough skin | FLG2 | 0.0001 | 63% | 72% | 53% | 0.25 | <144.1 |
| Uneven skin tone | TG3 | 0.2048 | 60% | 67% | 46% | 0.12 | <26.8 |
| Eye wrinkles | IDE | 0.0000 | 62% | 67% | 58% | 0.24 | <11.5 |
| Photo-aging | TG3 | 0.0243 | 57% | 66% | 48% | 0.14 | <24.9 |
| Loss of Elasticity | LCN1 | 0.0201 | 57% | 57% | 56% | 0.13 | >44.3 |
| Dilated pores | YKL40 | 0.2245 | 54% | 61% | 51% | 0.10 | >2.4 |

Preliminary studies have also suggested a link between biomarkers and whether a subject is a responder or a non-responder to retinol and proxylane. Preliminary clinical studies have suggested that the YKL40 and TG3 biomarkers indicate that a subject will be responsive to retinol for improvement of underneath eye wrinkles, that the TG3 and LCN1 biomarkers indicate that a subject will be responsive to retinol for improvement of full-face dyschromia, and that the YKL40 biomarker indicates that a subject will be responsive to proxylane for improvement of erythrosis. In some embodiments, the trend determination engine 214 uses one or more of these clinically suggested relationships and the biomarker concentration information to predict one or more facial aging trends based on the biomarker concentration information. In some embodiments, the trend determination engine 214 may update a life-time aging trend indicator based on the biomarker concentration information. In some embodiments, this life-time aging trend indicator may be stored by the trend visualization computing device 212. In some embodiments, the life-time aging trend indicator may be stored by a cloud service or other server computing device. In some embodiments, the life-time aging trend indicator may later be presented to show progress in addressing the predicted facial aging trends over time.

The method 400 then proceeds to block 408, where a trend visualization engine 216 of the trend visualization computing device 212 generates a trend visualization based on the at least one facial aging trend. In some embodiments, the trend visualization is a virtual representation, and the terms "trend visualization" and "virtual representation" may be used interchangeably. In some embodiments, the trend determination engine 214 may determine a degree to which the biomarker concentration information indicates the presence of one or more facial aging trends, and the trend visualization engine 216 may generate a trend visualization based on the indicated degrees. For example, if the biomarker concentration information indicates a 60% probability of the development of rough skin, the trend determination engine 214 will provide the 60% probability of rough skin to the trend visualization engine 216, and the trend visualization engine 216 generates the trend visualization based on the 60% probability of rough skin. In some embodiments, the trend determination engine 214 may determine a presence or absence of one or more facial aging trends instead of a probability, and may provide the facial aging trend information as one or more binary values to the trend visualization engine 216. In some embodiments, different trend visualizations may be generated based on the use of one or more skincare products. For example, a first trend visualization may be generated to show the currently detected trend, and a second trend visualization may be generated to show how the trend would be affected by the application of a specified skincare product over time.

In some embodiments, the trend visualization engine 216 may create a visualization that is based on probabilities received from the trend determination engine 214. For example, if the visualization is a graph visualization such as the spider diagram 302 illustrated in FIG. 3, the probability of each skin trend may be indicated as a value from zero (the center of the spider diagram 302) to 100 (the outer edge of the spider diagram 302). As another example, if the visualization is a manipulated version of a photo of the subject, the probability may be used to change the intensity of a filter applied to the photo, or to change an amount of time over which a change illustrated by the filter is intended to represent. Accordingly, a determined 60% probability of the appearance of wrinkles or fine lines may cause a filter to be applied and a photo visualization to be presented with an indication that it shows a predicted appearance after five years, while a determined 30% probability of the appearance of wrinkles or fine lines may cause a filter to be applied and a similar photo visualization to be presented, but with an indication that it shows a predicted appearance after ten years instead of five years. These values are examples only, and in some embodiments, different values or techniques may be used.

In some embodiments, more than one skin trend may be determined by the trend determination engine 214, and the trend visualization engine 216 may generate a combined trend visualization showing the effects of all of the skin trends. In some embodiments, the trend visualization engine 216 may generate separate visualizations for each detected skin trend. For example, the spider diagram 302 illustrated in FIG. 3 concurrently visualizes multiple predicted skin trends. As another example, a photo visualization on which filters are applied to show predicted trends may apply a single filter at a time to separately illustrate the predicted skin trends. As yet another example, multiple filters may be applied in sequence to a photo to concurrently illustrate multiple skin trends.

At block 410, the trend visualization computing device 212 presents the trend visualization on a display device 218 of the trend visualization computing device 218. In some embodiments, the trend visualization computing device 212 may instead transmit the trend visualization to another computing device for presentation or storage. For example, if the trend visualization computing device 212 is a server computing device, the trend visualization computing device 212 may generate the trend visualization and transmit it to a mobile computing device or a desktop computing device for presentation. In some embodiments, the transmission of the trend visualization between the devices may be encrypted and/or anonymized.

The method 400 then proceeds to an end block and terminates.

Figure 5:
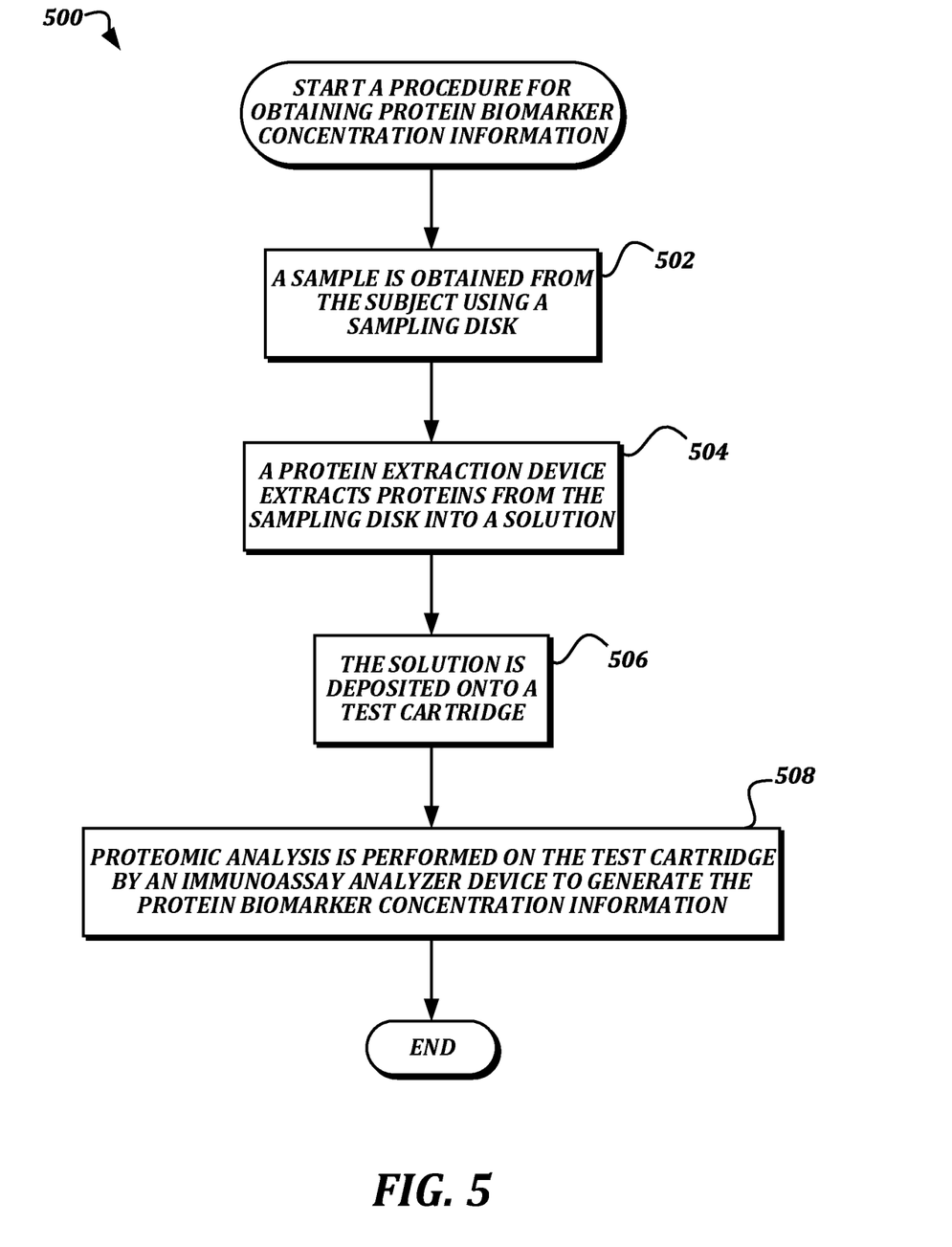
FIG. 5 is a flowchart that illustrates an example embodiment of a procedure for obtaining protein biomarker concentration information according to various aspects of the present disclosure.

FIG. 5 is a flowchart that illustrates an example embodiment of a procedure for obtaining protein biomarker concentration information according to various aspects of the present disclosure. The procedure 502 is a non-limiting example of a procedure suitable for use at block 402 of FIG. 4 for obtaining protein biomarker concentration information for a subject.

From a start block, the procedure 500 advances to block 502, where a sample is obtained from the subject using a sampling disk 204. In some embodiments, the sampling disk 204 may be attached to the skin of the subject via an adhesive. In some embodiments, the sampling disk 204 may absorb substances such as sweat, sebum, and other skin secretions. In some embodiments, the adhesive of the sampling disk 204 may collect skin cells from the skin of the subject. In some embodiments, the sampling disk 204 may be placed on the skin and removed from the skin multiple times to collect the skin sample. In some embodiments, a weight or pressure may be applied on top of the sampling disk 204, and/or the sampling disk 204 may be left in place for a specific amount of time, in order to obtain a consistent sample.

Next, at block 504, a protein extraction device 210 extracts proteins from the sampling disk into a solution. In some embodiments, the protein extraction device 210 may apply the solution to the sampling disk in order to dissolve the skin cells, skin secretions, or other sampled matter into the solution. In some embodiments, the sampling disk 204 may be placed in a buffer solution, and may then be shaken to cause the skin sample to be dissolved in the solution.

At block 506, the solution is deposited onto a test cartridge 206. In some embodiments, a droplet of the solution created by the protein extraction device 210 that includes the proteins from the sampling disk is placed in an inlet of the test cartridge 206. At block 508, proteomic analysis is performed on the test cartridge 206 by an immunoassay analyzer device 208 to generate the protein biomarker concentration information. In some embodiments, the test cartridge 206 is inserted into the immunoassay analyzer device 208, which uses laser light to measure the fluorescing beads and thereby determine the concentrations of the protein biomarkers in the skin sample. The procedure 500 then advances to an end block and terminates. The protein biomarker concentration information may be displayed on a screen of the immunoassay analyzer device 208, may be transmitted electronically to another device, or may be provided to another device in some other way in order to allow the protein biomarker concentration information to be used for predicting and/or visualizing future trends (or for any other purpose). If transmitted electronically to another device, the transmission may be encrypted and/or anonymized.

While illustrative embodiments have been illustrated and described, it will be appreciated that various changes can be made therein without departing from the spirit and scope of the invention.

The invention claimed is:

1. A method of generating a facial aging visualization of a subject, the method implemented by at least one computer processor programmed by one or more machine instructions, the method comprising:
   determining a predicted future presence of at least one clinical sign of aging for the subject based on receiving protein biomarker concentration information generated from a sample collected from the subject;
   generating a virtual representation on an electronic display indicative of the predicted future presence of the at least one clinical sign of aging in the absence of any treatment; and
   generating at least one virtual representation on the electronic display indicative of a predicted effect of at least one treatment on the predicted future presence of the at least one clinical sign of aging;
   wherein determining the predicted future presence of the at least one clinical sign of aging for the subject based on receiving protein biomarker concentration information generated from the sample collected from the subject includes determining the predicted future presence of the at least one clinical sign of aging based on receiving information about a concentration of or information indicative of a presence or absence of at least one of an FLG2 biomarker, a TG3 biomarker, an IDE biomarker, and a YKL40 biomarker.

2. The method of claim 1, further comprising updating a life-time aging trend indicator based on receiving protein biomarker concentration information.

3. The method of claim 1, further comprising receiving one or more inputs indicative of protein biomarker concentration information from an immunoassay analyzer device.

4. The method of claim 1, wherein determining the predicted future presence of the at least one clinical sign of aging for the subject based on receiving protein biomarker concentration information generated from the sample collected from the subject includes determining the predicted future presence of at least one of shiny skin, rough skin, uneven skin tone, eye wrinkles, photo-aging, loss of elasticity, or dilated pores based on receiving the protein biomarker concentration information.

5. The method of claim 1, wherein generating the virtual representation on an electronic display indicative of the predicted future presence of the at least one clinical sign of aging includes generating a spider diagram or a face aging simulation.

6. The method of claim 1, wherein the method further comprises receiving one or more questionnaire responses, and wherein the determination of the predicted future presence of the at least one clinical sign of aging is further based on the one or more questionnaire responses.

7. A system for generating a facial aging visualization of a subject, the system comprising:
- circuitry for determining a predicted future presence of at least one clinical sign of aging for the subject based on receiving protein biomarker concentration information generated from a sample collected from the subject; and
- circuitry for generating a virtual representation on an electronic display indicative of the predicted future presence of the at least one clinical sign of aging, wherein the virtual representation includes a rate of change of the clinical sign of aging;
- wherein the circuitry for determining the predicted future presence of the at least one clinical sign of aging for the subject based on receiving protein biomarker concentration information generated from the sample collected from the subject includes circuitry for determining the predicted future presence of the at least one clinical sign of aging based on receiving information about a concentration of or information indicative of a presence or absence of at least one of an FLG2 biomarker, a TG3 biomarker, an IDE biomarker, and a YKL40 biomarker.

8. The system of claim 7, further comprising circuitry for updating a life-time aging trend indicator based on receiving protein biomarker concentration information.

9. The system of claim 7, further comprising circuitry for receiving one or more inputs indicative of protein biomarker concentration information from an immunoassay analyzer device.

10. The system of claim 7, wherein the circuitry for determining the predicted future presence of the at least one clinical sign of aging for the subject based on receiving protein biomarker concentration information generated from the sample collected from the subject includes circuitry for determining the predicted future presence of at least one of shiny skin, rough skin, uneven skin tone, eye wrinkles, photo-aging, loss of elasticity, or dilated pores based on receiving protein biomarker concentration information.

11. The system of claim 7, wherein the circuitry for generating the virtual representation indicative of the predicted future presence of the at least one clinical sign of aging includes circuitry for generating a spider diagram or a face aging simulation.

12. The system of claim 7, further comprising circuitry for receiving one or more questionnaire responses, wherein the circuitry for determining the predicted future presence of the at least one clinical sign of aging for the subject based on receiving protein biomarker concentration information generated from the sample collected from the subject is configured to further base the determination of the predicted future presence of the at least one clinical sign of aging on the one or more questionnaire responses.

13. A computing device configured to:
- determine a predicted future presence of at least one clinical sign of aging for a subject based on receiving protein biomarker concentration information generated from a sample collected from the subject;
- determine a first predicted effect of a first treatment regimen on the predicted future presence of the at least one clinical sign of aging:
- determine a second predicted effect of a second treatment regimen on the predicted future presence of the at least one clinical sign of aging: and
- generate a first virtual representation on an electronic display indicative of the first predicted effect of the first treatment regimen on the predicted future presence of the at least one clinical sign of aging: and
- generate a second virtual representation on an electronic display indicative of the second predicted effect of the second treatment regimen on the predicted future presence of the at least one clinical sign of aging;
- wherein determining the predicted future presence of the at least one clinical sign of aging for the subject based on receiving protein biomarker concentration information generated from the sample collected from the subject includes determining the predicted future presence of the at least one clinical sign of aging based on receiving information about a concentration of or information indicative of a presence or absence of at least one of an FLG2 biomarker, a TG3 biomarker, an IDE biomarker, and a YKL40 biomarker.

14. The computing device of claim 13, further configured to update a life-time aging trend indicator based on receiving protein biomarker concentration information.

15. The computing device of claim 13, further configured to receive one or more inputs indicative of protein biomarker concentration information from an immunoassay analyzer device.

16. The computing device of claim 13, wherein determining the predicted future presence of the at least one clinical sign of aging for the subject based on receiving protein biomarker concentration information generated from the sample collected from the subject includes determining a predicted future presence of at least one of shiny skin, rough skin, uneven skin tone, eye wrinkles, photo-aging, loss of elasticity, or dilated pores based on receiving the protein biomarker concentration information.

17. The computing device of claim 13, wherein at least one of generating the first virtual representation on the electronic display and generating the second virtual representation on the electronic display includes generating at least one spider diagram or at least one face aging simulation.

* * * * *